United States Patent [19]

Bell et al.

[11] 4,248,784

[45] Feb. 3, 1981

[54] PYRROLE-3-ACETAMIDES

[75] Inventors: Malcolm R. Bell; Rudolf Oesterlin, both of East Greenbush, N.Y.

[73] Assignee: Sterling Drug Inc., New York, N.Y.

[21] Appl. No.: 772,004

[22] Filed: Feb. 25, 1977

[51] Int. Cl.$^3$ .......................................... C07D 207/337
[52] U.S. Cl. .............................. 260/326.2; 260/326.47; 424/274
[58] Field of Search ........................ 260/326.2, 326.47

[56] References Cited

U.S. PATENT DOCUMENTS 3,247,222  4/1966  Lunsford .......................... 260/326.47

FOREIGN PATENT DOCUMENTS 1406330  9/1975  United Kingdom .................. 260/326.2

OTHER PUBLICATIONS

Herz et al., J. Org. Chem. vol. 24, pp. 201–204 (1959).
Thielheimer, Synthetic Methods of Organic Chemistry, vol. 12, 190, 250, vol. 13, 267, vol. 16, 263, 263a, vol 18, 249.
Gillet et al., Eur. J. Med. Chem. Chemica Therapeutica, vol. 11, 173–181 (1976).
Lambelin et al., Chem. Abs., vol. 79: 78604a (1973).

*Primary Examiner*—Mary C. Lee
*Attorney, Agent, or Firm*—William G. Webb; B. Woodrow Wyatt

[57] ABSTRACT

1-$R_1$-4-$R_4$-$\alpha,\alpha$,2,5-Tetramethylpyrrole-3-acetamides, useful as anti-secretory and anti-ulcer agents, are prepared by hydrolysis, in the presence of a dilute mineral acid, of a corresponding 1-$R_1$-4-$R_4$-$\alpha,\alpha$,2,5-tetramethylpyrrole-3-acetonitrile.

4 Claims, No Drawings

PYRROLE-3-ACETAMIDES

BACKGROUND OF THE INVENTION (a) Field of the Invention

This invention relates to 1-$R_1$-4-$R_4$-$\alpha,\alpha$,2,5-tetramethylpyrrole-3-acetamides useful as anti-secretory and antiulcer agents.

(b) Description of the Prior Art

The compound, 1-(4-chlorophenyl)-2,5,-dimethylpyrrole-3-acetamide, is described by Gillet et al., Eur. J. Med. Chem. Chimica Therapeutiea 11, 173-181 (1976) along with a number of 1-substituted-2,5-dimethylpyrrole-3-acetic acids as possible anti-inflammatory and analgesic agents. Although the acids are shown by data presented to have the desired anti-inflammatory and analgesic activities, the above-indicated amide was found to be inactive as an analgesic agent at doses as high as 400 mg./kg. on intraperitoneal administration, but no data is given by the reference of results of anti-inflammatory activity tests.

The same general disclosure of the acids is found in British Pat. No. 1,406,330, published Sept. 17, 1975, assigned to Continental Pharma, where the work reported in the above-mentioned Gillet publication was carried out. The disclosure in British Pat. No. 1,406,330 is thus essentially cumulative to that in the Gillet publication. However, although the British patent generically describes a genus of 2,5-di-lower-alkyl-1-substituted-pyrrole-3-acetamides embracive of the above-named 1-(4-chlorophenyl)-2,5-dimethylpyrrole-3-acetamide as intermediates for preparing the corresponding pyrrole-3-acetic acids, which themselves are stated to be useful as analgesics and anti-inflammatory agents, the patent in fact specifically discloses no amides at all.

Thus so far as the presently known art reveals, 1-(4-chlorophenyl)-2,5-dimethylpyrrole-3-acetamide has no known utility.

SUMMARY OF THE INVENTION

In a composition of matter aspect, the invention relates to certain 1-$R_1$-4-$R_4$-$\alpha,\alpha$,2,5-tetramethylpyrrole-3-acetamides which are useful as anti-secretory and antiulcer agents.

In a process aspect, the invention relates to a process for preparing 1-$R_1$-4-$R_4$-$\alpha,\alpha$,2,5-tetramethylpyrrole-3-acetamides which comprises hydrolyzing, with an aqueous mineral acid, a corresponding 1-$R_1$-4-$R_4$-$\alpha,\alpha$,2,5-tetramethylpyrrole-3-acetonitrile.

DETAILED DESCRIPTION INCLUSIVE OF THE PREFERRED EMBODIMENTS

More specifically, the invention relates to compounds having the formula:

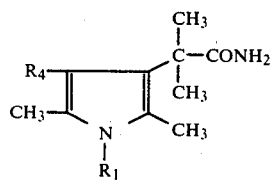

where $R_1$ is methyl or phenyl and $R_4$ is hydrogen or methyl useful as anti-secretory and anti-ulcer agents, and which are chemically designated 1-$R_1$-4-$R_4$-$\alpha,\alpha$,2,5-tetramethylpyrrole-3-acetamides.

The compounds of formula I are prepared by hydrolyzing, with an aqueous mineral acid, a corresponding 1-$R_1$-4-$R_4$-$\alpha,\alpha$,2,5-tetramethylpyrrole-3-acetonitrile of formula II:

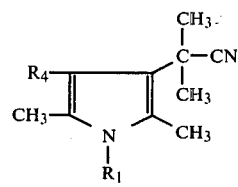

where $R_1$ and $R_4$ have the meanings given above. The hydrolysis is carried out by refluxing the nitrile in the aqueous acid while following the course of the reaction using thin layer chromatography. The reaction is usually complete in from five to ten hours at ambient temperature or in from five to fifteen minutes at 80°-85° C. Suitable mineral acids are phosphoric acid, polyphosphoric acid or sulfuric acid. A preferred mineral acid is sulfuric acid, and it is preferred to use 1 ml. of concentrated sulfuric acid per millimole of the nitrile, diluting the acid with sufficient water to make a solution 90% in sulfuric acid V/V, i.e. 0.1 ml. of water per ml. of sulfuric acid.

The intermediate 1-$R_1$-4-$R_4$-$\alpha,\alpha$,2,5-tetramethylpyrrole-3-acetonitriles of formula II are in turn prepared by reacting a 1-$R_1$-4-$R_4$-2,5-dimethylpyrrole of formula III:

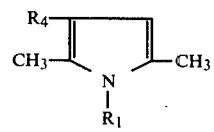

where $R_1$ and $R_4$ have the meanings given above with acetone, an alkali metal cyanide and an alkali metal acetate in excess acid, for example glacial acetic acid or trifluoroacetic acid. The reaction is advantageously carried out by refluxing a mixture of the pyrrole under a nitrogen atmosphere with two molar equivalents each of acetone and the alkali metal nitrile and one molar equivalent of the alkali metal acetate in an excess of the acid, while following the course of the reaction using thin layer chromatography. The reaction is usually complete in twelve to twenty-four hours, although the preparation of the nitrile of formula II where $R_4$ is hydrogen requires a somewhat longer reaction time. Preferred acids are acetic acid and trifluoroacetic acid.

Alternatively the compounds of formula II can be prepared by reaction of the 1-$R_1$-4-$R_4$-2,5-dimethylpyrroles of formula III with two molar equivalents of 2-amino-2-methylpropionitrile:

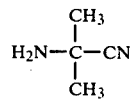

(described in U.S. Pat. No. 4,008,250) in place of the acetone and alkali metal cyanide but otherwise using the same reaction conditions as described above.

The 1-$R_1$-4-$R_4$-2,5-dimethylpyrroles of formula III are known compounds.

In standard biological test procedures, described generally by Shay et al., Gastroenterology 5, 43 (1945) and 26, 906 (1954), the compounds of formula I have been found to possess anti-secretory and anti-ulcer activities when administered to rats and are thus useful as anti-secretory and anti-ulcer agents. The anti-secretory and anti-ulcer test procedures used are also fully described in detail in U.S. Pat. No. 4,008,250, patented Feb. 15, 1977.

The compounds of formula I were thus found to inhibit secretion of gastric fluids and to inhibit reserpine-induced stomach ulceration when administered orally (p.o.), intraperitoneally (i.p.) or introduodenally (i.d.) at a dose range from around 25 mg./kg. to around 100 mg./kg. The compounds are preferably administered orally, and the amount of a particular compound to be administered, either alone or as the essential active ingredient in a formulation, will range from about 25 to about 100 mg./kg.

The actual determination of the numerical biological data definitive for a particular compound of formula I is readily determined by standard test procedures by technicians versed in pharmacological test procedures without the need for any extensive experimentation.

The compounds of formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were established on the basis of study of their infrared, ultraviolet, and NMR spectra, and confirmed by the correspondence between calculated and found values for elementary analyses for the elements. The course of reaction and homogeneity of the products were ascertained by thin layer chromatography.

The manner and process of making and using the invention, and the best mode contemplated by the inventors of carrying out the invention will now be described so as to enable any person skilled in the art to which it pertains to make and use the same. The melting points are uncorrected.

PREPARATION OF INTERMEDIATES OF FORMULA II

Preparation I

A mixture of 54.5 g. (0.5 mole) of 1,2,5-trimethylpyrrole [Kreutzberger et al., J. Org. Chem. 26, 3790–3796 (1961)], 58 g. (1 mole) of acetone, 65 g. (1 mole) of potassium cyanide and 46 g. (0.5 mole) of potassium acetate in 200 ml. of glacial acetic acid was heated under reflux in a nitrogen atmosphere with stirring for forty-eight hours and then poured into an ice/water mixture. Extraction of the mixture with diethyl ether followed by washing of the extracts successively with water, aqueous sodium bicarbonate and brine, drying over anhydrous sodium sulfate and evaporation to dryness afforded an oil which was distilled in vacuo to give 48.7 g. (55% ) of $\alpha,\alpha,1,2,5$-pentamethylpyrrole-3-acetonitrile, b.p. 105°–107° C./0.08–0.1 mm., as a clear yellow oil which crystallized on standing.

Following a procedure similar to that described in Preparation 1, the following 1-$R_1$-4-$R_4$-$\alpha,\alpha$,2,5-tetramethylpyrrole-3-acetonitriles of formula II were also prepared.

PREPARATION 2

Reaction of 52 g. (0.304 mole) of 1-phenyl-2,5-dimethylpyrrole [Hazlewood et al., J. Proc. Roy. Soc. N. S. Wales 71, 92–102 (1937); C. A. 32, 1696[3] (1938)] with 36 g. (0.608 mole) of acetone, 39 g. (0.608 mole) of potassium cyanide and 28 g. (0.304 mole) of potassium acetate in 150 ml. of glacial acetic acid, refluxing the mixture for twenty-four hours, afforded 30.5 g. (42%) of 1-phenyl-$\alpha,\alpha$,2,5-tetramethylpyrrole-3-acetonitrile, b.p. 103°–121° C./0.1–0.2 mm., as a viscous pale yellow oil.

PREPARATION 3

Reaction of 50 g. (0.27 mole) of 1-phenyl-2,4,5-trimethylpyrrole (alternatively named 1-phenyl-2,3,5-trimethylpyrrole) [Buu-Hoi, J. Org. Chem. 24, 372–374 (1959)] with 29 g. (0.54 mole) of acetone, 35.5 g. (0.54 mole) of potassium cyanide and 26.6 g. (0.27 mole) of potassium acetate in 120 ml. of glacial acetic acid, refluxing the mixture for seven days, afforded 14 g. (21%) of 1-phenyl-$\alpha,\alpha$,2,4,5-pentamethylpyrrole-3-acetonitrile, b.p. 127°–129°./0.06 mm. as a viscous pale yellow oil. (In order to attempt to shorten the reaction time in this preparation, the reaction was interrupted at the end of three days refluxing, and 1.2 molar equivalents of 2-amino-2-methylpropionitrile and an additional 50 ml. of glacial acetic acid were added. There was no detectable increase in the reaction rate as determined by thin layer chromatography.)

PREPARATION OF THE FINAL PRODUCTS OF FORMULA I

EXAMPLE 1

A mixture of 48.7 g. (0.276 mole) of $\alpha,\alpha$,1,2,5-pentamethylpyrrole-3-acetonitrile in a solution of 25 ml. of water and 250 ml. of concentrated sulfuric acid was heated on a steam bath with stirring at about 85° C. for five minutes. The mixture was then poured into an ice/water mixture and neutralized with 35% aqueous sodium hydroxide. The gum which separated solidified on standing. It was taken into ethyl acetate and the solution washed successively with water and brine, dried over anhydrous sodium sulfate and taken to dryness to give 37 g. of product which was recrystallized from ethyl acetate/hexane. There was thus obtained 18.5 g. (34%) of $\alpha,\alpha$,1,2,5-pentamethylpyrrole-3-acetamide, m.p. 96°–98° C.

Following a procedure similar to that described in Example 1, the following 1-$R_1$-4-$R_4$-$\alpha,\alpha$,2,5-tetramethylpyrrole-3-acetamides of formula I were also prepared.

EXAMPLE 2

Hydrolysis of 30.5 g. (0.128 mole) of 1-phenyl-$\alpha,\alpha$,2,5-tetramethylpyrrole-3-acetonitrile with a solution of 13 ml. of water and 130 ml. of concentrated sulfuric acid, the reaction mixture being heated at 80° C. for ten minutes and recrystallization of the product from cyclohexane gave 19.6 g. (60%) of 1-phenyl-$\alpha,\alpha$,2,5-tetramethylpyrrole-3-acetamide, m.p. 131°–133° C.

EXAMPLE 3

Hydrolysis of 14 g. (0.055 mole) of 1-phenyl-$\alpha,\alpha$,2,4,5-pentamethylpyrrole-3-acetonitrile with a solution of 6 ml. of water and 60 ml. of concentrated sulfuric acid, the reaction being carried out at ambient temperature for five hours, and recrystallization of the product from ethyl acetate gave 5.5 g. (37%) of 1-phenyl-$\alpha,\alpha$,2,4,5-pentamethylpyrrole-3-acetamide, m.p. 154°–156.5° C.

BIOLOGICAL TEST RESULTS

Date obtained on administration (oral - p.o., intraperitoneal - i.p. or intraduodenal - i.d.) in rats of the compounds of formula I in the anti-secretory and anti-ulcer tests are given in the table below in terms of the pH of medicated vs. control rats and the percent increase in pH over control animals (anti-secretory test) and in terms of the number of medicated animals with ulcers vs. the number of control animals with ulcers and the percent of total animals over control without ulcers (anti-ulcer test). Doses are expressed in mg./kg. of body weight. Compounds are considered active in either test if any measurable increase in the pH of gastric fluid or decrease in ulcer score over controls are obtained, although for purposes of further evaluation for possible ultimate commercial development, compounds were not considered further unless an increase in pH of 80% over controls is obtained in the anti-secretory test or a reduction of 30% over controls is obtained in the anti-ulcer test. The compounds are identified by the example number above where their preparations are described.

| Ex. | Dose | Anti-Secretory | | Anti-Ulcer | |
|---|---|---|---|---|---|
| | | pH Med./ pH Cont. | % Decrease | No. with Ulcers/Cont. | % Decrease |
| 1 | 50 (p.o.) | — | — | 4/5 | 20 |
| | 100 (p.o.) | 1.5/1.0 | 50 | 1/10 | 10 |
| 2 | 25 (p.o.) | — | — | 3/5 | 40 |
| | 50 (p.o.) | — | — | 0/10 | 100 |
| | 100 (p.o.) | 1.5/1.0 | 50 | 0/10 | 100 |
| 3 | 50 (i.d.) | 3.4/1.4 | 143 | — | — |
| | 50 (i.p.) | 5.3/1.2 | 342 | — | — |
| | 100 (p.o.) | 3.5/1.2 | 192 | 0/10 | 100 |

We claim:

1. A compound having the formula:

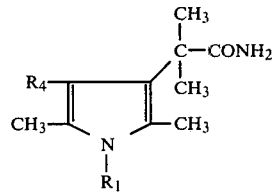

where $R_1$ is methyl or phenyl and $R_4$ is hydrogen or methyl.

2. $\alpha,\alpha$,1,2,5-Pentamethylpyrrole-3-acetamide according to claim 1.

3. 1-Phenyl-$\alpha,\alpha$,2,5-tetramethylpyrrole-3-acetamide according to claim 1.

4. 1-Phenyl-$\alpha,\alpha$,2,4,5-pentamethylpyrrole-3-acetamide according to claim 1.

* * * * *